United States Patent [19]

Goralski et al.

[11] Patent Number: 4,895,996
[45] Date of Patent: Jan. 23, 1990

[54] SYNTHESIS OF ALKENES FROM ENAMINES VIA HYDROBORATION

[75] Inventors: Christian T. Goralski, Midland, Mich.; Bakthan Singaram; Herbert C. Brown, both of West Lafayette, Ind.

[73] Assignees: Purdue Research Foundation, West Lafayette, Ind.; The Dow Chemical Company, Midland, Mich.

[21] Appl. No.: 258,744

[22] Filed: Oct. 17, 1988

[51] Int. Cl.$^4$ ............................................... C07C 1/32
[52] U.S. Cl. .................................. 585/328; 585/318; 585/357; 585/638
[58] Field of Search ................ 585/318, 328, 357, 638

[56] References Cited

PUBLICATIONS

Christian T. Goralski et al., "Stereospecific Synthesis of Pure[Z]-and [E]-Alkenes from Enamines via Hydroboration," Presented to National American Chemical Society Meeting, Toronto, Canada (Jun. 1988).

Christian T. Goralski et al., "Hydroboration. 81. Synthesis of 2-(Dialkylamino)Boronic Esters and Acids via Hydroboration of Enamines. A Convenient Preparation of β-Dialkylamino Alcohols," The Journal of Organic Chemistry, vol. 52, 1987, pp. 4104–4019.

J. W. Lewis et al., "Hydrogenolysis of Enamines. Part II. Hydroboration-Protonolysis," J. Chem. Soc. (B) Phys. Org., 1969, pp. 863–867.

J. W. Lewis et al., "Alkenes from Enamines via Hydroboration," Tetrahedron Letters No. 30, 1964, pp. 2039–2042.

Daniel J. Pasto et al., "Transfer Reactions Involving Boron. IX. Mechanism of Product Formation in the Hydroboration of Vinyl Halides,." J. Org. Chem. vol. 31, Sep. 1966, pp. 2773–2777.

Daniel J. Pasto et al., "Transfer Reactions Involving Boron. X. The Stereochemistry of Eliminations Involving β-Substituted Organoboranes," J. Org. Chem., vol. 31, Sep. 1966, pp. 2777–2784.

Gerald L. Larson et al., "A Synthesis of Olefins via Hydroboration of Cyclic Trimethylsilyl Enol Ethers," Tetrahedron Letters No. 46, 1975, pp. 4005–4008.

Gilbert Stork et al., "The Enamine Alkylation and Acylation of Carbonyl Compounds," The Journal of the American Chemical Society, vol. 85, Jan. 20, 1963, pp. 207–222.

*Primary Examiner*—Curtis R. Davis
*Attorney, Agent, or Firm*—Paula Sanders Ruhr

[57] ABSTRACT

Alkenes are prepared by the hydroboration of enamines followed by an elimination reaction to form the alkene. This process has wide applicability and is useful for the stereospecific synthesis of [Z] isomers. It is preferred to use 9-borabicyclo[3.3.1 nonane as the hydroborating agent and to use methanol to catalyze the elimination reaction.

19 Claims, No Drawings

SYNTHESIS OF ALKENES FROM ENAMINES VIA HYDROBORATION

BACKGROUND OF THE INVENTION

The current invention relates to the synthesis of unsaturated hydrocarbyl compounds such as alkenes from enamines via hydroboration.

Lewis et al., *J. Chem. Soc. (B)*, 1969, 863 teach that enamines prepared from ketones can be subjected to hydroboration followed by hydrolysis in acetic acid to form the corresponding aminoboronic acid. The boronic acid, upon heating to reflux, undergoes elimination to produce the corresponding alkenes. Borane is taught to be useful as the hydroborating agent and generally the hydroboration is conducted at reduced temperatures.

Pasto et al., *J. Org. Chem.* 1966, 31, 2777 discuss the uncatalyzed, base catalyzed and acid catalyzed elimination reactions of organoboranes to form alkenes. The use of a mixture of tri-n-propylboron, di-n-propyldeuterioborane, mono-n-propyldideuterioborane and deuterioborane as a hydroborating agent is discussed.

Larson et al., *Tetrahedron Letters*, 1975, 4005 discuss the synthesis of alkenes via the hydroboration of cyclic trimethylsilyl enol ethers. The stereospecific synthesis of unsymmetrical cyclic alkenes is taught to be possible when single isomers of the trimethylsilyl enol ethers are available as starting materials.

The existing methods for the preparation of alkenes are not without problems. Problems include the limitations on the type of alkenes that may be prepared and the necessity of harsh reaction conditions. Thus, what is needed is a simple process for the preparation of alkenes that operates under mild conditions; that has applicability for the preparation of a wide variety of alkenes, both cyclic and acyclic; and that has utility for the preparation of stereospecific isomers.

SUMMARY OF THE INVENTION

The present invention is such a process for preparing a wide variety of alkenes, including cyclic and acyclic alkenes, heterocyclic alkenes, terminal alkenes and dienes, consisting essentially of two essential steps of (1) reacting an enamine wherein the enamine has an alkene portion which corresponds to an alkene selected from the group comprising cyclic alkenes, heterocyclic alkenes, acyclic alkenes, terminal alkenes, and dienes with a hydroborating agent under reaction conditions sufficient to form an intermediate organoborane; and (2) subjecting the organoborane formed in step (1) to an elimination reaction under reaction conditions sufficient to form the alkene corresponding to the alkene portion of the starting enamine.

When the alkene so formed is capable of existing as [E] or [Z] isomers, the [Z] isomer is formed essentially to the exclusion of the [E] isomer.

It is surprising that the process of this invention results in the formation of a single stereo-specific isomer rather than in the formation of a mixture of isomers. It is also surprising that the process is useful for the formation of substituted or unsubstituted cycloalkenes, acyclic alkenes, terminal alkenes, dienes and heterocyclic alkenes in which the heteroatom is oxygen, sulfur or substituted nitrogen.

The alkenes formed by the process of this invention are known compounds having a wide variety of uses. The compounds are generally useful in organic synthesis and in the preparation of polymers.

DETAILED DESCRIPTION OF THE INVENTION

The enamine starting materials useful in the practice of this invention are alkenyl amines wherein an amine nitrogen and an alkenyl carbon are covalently bonded. When the enamine starting materials may exist as stereoisomers, it is preferred that the isomer having the [E] configuration is used. In the enamine, the [E] configuration corresponds to the following

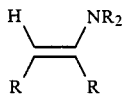

FIG. 1 wherein R represents a hydrocarbyl group or groups. It should be understood that in the situation where a diene is prepared by the process of this invention, the stereochemistry of the double bond removed from the amine nitrogen of the enamine is not affected.

The alkene portion of the enamines useful in the practice of this invention may include substituted or unsubstituted cyclic or heterocyclic alkenes, substituted or unsubstituted linear alkenes, and substituted or unsubstituted dienes.

Enamines useful in the practice of this invention may, in some cases, be obtained commercially or may be prepared by the reaction of a secondary amine and a carbonyl compound. Carbonyl compounds useful in the preparation of the enamines useful in the practice of this invention include cyclic ketones, acyclic ketones, aldehydes, unsaturated aldehydes and heterocyclic ketones containing at least one heteroatom selected from the group comprising oxygen, sulfur, N-alkyl and N-aryl. The carbonyl compounds may be unsubstituted or may contain inert substituents. For purposes of this invention, inert substituents are those which will not interfere with the formation of the enamines, the hydroboration of the enamines so formed or the subsequent elimination reactions to form alkenes. Examples of suitable inert substituents include alkyl, aryl, alkoxy, alkylthio, and heteroaryl such as thiophene and pyridine.

Non-limiting examples of useful ketones include cyclopentanone, cyclohexanone, 2-methylcyclohexanone, 4-tertiary butyl cyclohexanone, 3,3,5,5-tetramethylcyclohexanone, cycloheptanone, cyclooctanone, 2-phenylcyclohexanone, tetrahydropyran-4-one, tetrahydrothiopyran-4-one and 1-benzyl-4-piperidone.

Also useful as starting materials in the preparation of the enamines useful in the practice of this invention are aldehydes, which include as non-limiting examples, 3-phenylpropionaldehyde, 1-octanal, 10-undecene-1-al, [Z]-4-decene-1-al and [E]-4-decene-1-al. Another group of compounds useful as starting materials in the preparation of enamines useful in this invention are ketals such as 1,4-cyclohexanedione monoethylene ketal.

The carbonyl compounds are reacted with amines to prepare the enamines which undergo hydroboration in the practice of this invention. Secondary amines are useful for this purpose. The secondary amines useful in the preparation of the enamines may be cyclic or acyclic and may be substituted or unsubstituted. Non-limiting examples of useful secondary amines include pyrrolidine, piperidine, hexamethyleneimine, morpholine, benzylmethylamine and di-lower alkyl amines.

The enamines are prepared by methods known in the art such as the method described by Stork et al., *J. A. C. S.*, 1963, 85, 207 which is incorporated herein by reference. Generally, enamines are prepared by the reaction of an aldehyde or ketone with a secondary amine in the presence of a dehydrating agent such as anhydrous potassium carbonate. Under these conditions, the ketones are converted directly into their enamines. Aldehydes are generally changed into the nitrogen analog of an acetal which then decomposes on distillation to form the enamines and a secondary amine.

Hydroborating agents useful in the process of this invention include borinane and di-substituted boranes. Preferably the di-substituted boranes correspond to the formula

$$R^1R^2BH \qquad (I)$$

wherein $R^1$ and $R^2$ are separately in each occurrence a $C_{5-20}$ hydrocarbyl. The hydrocarbyl may be branched or linear, aliphatic or alicyclic or $R^1$ and $R^2$ may join to form a multicyclic substituent. It is preferred that $R^1$ and $R^2$ are the same and are branched aliphatic or alicyclic or that $R^1$ and $R^2$ join to form a multicyclic substituent. It is most preferred that $R^1$ and $R^2$ join to form a multicyclic substituent.

As is well recognized by one skilled in the art, the substituted boranes useful in the practice of this invention typically occur as dimers rather than monomers although, for the sake of convenience, they are often described as if they were monomers. Thus, the hydroborating agents useful in the process of this invention also correspond to the formula

wherein $R^1$ and $R^2$ are as described above.

Non-limiting examples of hydroborating agents useful in the practice of this invention include 9-borabicyclo[3.3.1]nonane (9-BBN), dicyclohexyl borane, diisoamyl borane and borinane.

The hydroboration reaction in the practice of this invention is conducted under mild conditions. Temperatures useful in the practice of this invention are any under which the reaction will occur. Preferably temperatures are at least about $-20°$ C. and no greater than about 25° C. It is more preferred to conduct the hydroboration at room temperature or about 25° C. Pressures useful in the practice of this invention are any under which the reaction will proceed and may include subatmospheric or superatmospheric. It is preferred to conduct the hydroboration reaction at about atmospheric pressure for the sake of convenience.

The enamine and hydroborating agent may be mixed in any relative amounts which will permit the reaction to proceed. While larger or smaller ratios may be used, it is preferred that the molar ratio of enamine to hydroborating agent is at least about 0.9:1.0 and no greater than about 1.2:1.0. It is more preferred that the ratio is from about 1.1:1.0 to about 1.0:1.1.

The enamine and hydroborating agent are advantageously contacted in the presence of a solvent. Suitable solvents include, as non-limiting examples, ethers, such as di-lower alkyl ethers and cyclic ethers, and diols.

Examples of suitable solvents include dimethyl ether, diethyl ether, tetrahydrofuran and diethylene glycol dimethyl ether (diglyme). Preferred solvents include dimethyl ether and tetrahydrofuran (THF).

The hydroboration reaction is allowed to proceed until at least about 95 percent of the enamine is converted to an organoborane. It is preferred that the reaction proceed at least about one hour. It is also preferred that the reaction proceed no longer than about 24 hours and more preferred that it proceed no longer than about 12 hours. It is most preferred that the reaction proceed no longer than about 6 hours. Thus, the most preferred reaction time is from at least about 1 hour to no greater than about 6 hours.

The organoborane prepared as described above undergoes an elimination reaction to form an alkene. The new alkene corresponds to the alkene portion of the original enamine. The elimination may occur spontaneously. For example, the organoborane formed as described above undergoes an elimination reaction to form an alkene upon stirring over a period of time. The time required for uncatalyzed elimination is preferably no greater than about 500 hours and more preferably no greater than about 200 hours.

The elimination reaction is preferably catalyzed by the addition of an electron-donating compound. Non-limiting examples of reagents which catalyze the elimination reaction include lower alkanols, water and sodium hydroxide. It is preferred that methanol is used as the catalyst. The amount of catalyst is any that will result in a more facile elimination reaction. It is preferred that at least about one mole and no more than about 1.1 moles of the catalyst is used per mole of organoborane. It is most preferred that one molar equivalent of the catalyst is used for each mole of organoborane.

When a catalyst is used in the elimination step, it is preferred that the time of the elimination step is at least about ten minutes and no more than about two hours. It is more preferred that the time of reaction is about one hour.

Temperatures used in the elimination step are preferably at least about 25° C. Temperatures are also preferably maintained at no greater than about the boiling point of the electron-donating catalyst. The elimination step preferably occurs in the absence of external heating. However, in some cases the reaction mixture may be gently warmed to cause the elimination step to occur more quickly. If gentle warming is used, it is preferred that the reaction mixture be warmed to no more than about 50° C., more preferably no more than about 35° C.

When the structure of an alkene formed by the practice of this invention is capable of existing as [Z] and [E] isomers, the [Z] isomer is formed to the essential exclusion of the [E] isomer. The stereochemical purity of the [Z] isomer so formed is preferably at least about 99 percent.

A wide variety of alkenes are produced by the process of this invention. Examples of alkenes produced include cyclic and acyclic alkenes, heterocyclic alkenes, terminal alkenes and dienes. When dienes are produced by the process of this invention, the reaction occurs preferentially at the double bond to the carbon bonded to the nitrogen atom. The unsaturation further removed from the nitrogen atom, whether terminal, [E] or [Z], is not affected.

In a preferred embodiment of this invention, an equimolar portion of an enamine is added to 9-BBN in tetrahydrofuran (THF) and the mixture is stirred at room temperature for 1–6 hours. The THF is removed under vacuum and a portion of methanol equimolar to the starting enamine and 9-BBN is added. The product is recovered by distillation and any methanol remaining with the product is removed by techniques known to one skilled in the art.

ILLUSTRATIVE EMBODIMENTS

The following examples are given to illustrate the invention and should not be interpreted as limiting it in any way. Unless stated otherwise, all parts and percentages are given by weight.

EXAMPLE 1

Preparation of Cyclohexene

To a stirred suspension of 2.44 g (20.0 mmoles) of 9-borabicyclo[3.3.1]nonane (9-BBN) in 2 ml of tetrahydrofuran (THF) at 25° C. is added 3.34 g (20.0 mmoles) of 1-morpholinocyclohexene. After two hours at 25° C., the reaction mixture becomes a clear solution. The absence of 9-BBN in the reaction solution is confirmed by $^{11}B$ NMR spectroscopy.

The THF is removed under a pressure of 12 Torr. The reaction flask is then fitted with a distillation head and 0.64 g (20.0 mmoles) of methanol is added. A mildly exothermic reaction occurs and the reaction mixture solidifies. The solid is melted with heating and cyclohexene and methanol are collected by distillation at atmospheric pressure. The methanol is removed from the distillate by treatment of the distillate with 1.0 g of anhydrous calcium chloride. The product, 1.84 g of cyclohexene, is purified by distillation. This is a yield of 84 percent based on the 1-morpholinocyclohexene. It is identified by its melting point of 80° C.–82° C. at 745 Torr.

EXAMPLE 2

The procedure outlined above is followed changing the identity of the enamine and thus that of the alkene produced in each case. The yield of the alkene based on the starting enamine produced is shown in each case. The results obtained are shown in Table I below.

TABLE I

| Enamine | Alkene | % Yield |
|---|---|---|
| 1-morpholinocyclopentene | cyclopentene | 82 |
| 1-morpholinocyclohexene | cyclohexene | 84 |
| 1-piperidinocyclohexene | cyclohexene | 80 |
| 1-(N-methyl-N-benzylamino)cyclohexene | cyclohexene | 75 |
| 1-(hexamethyleneimino)cyclohexene | cyclohexene | 75 |

TABLE I-continued

| Enamine | Alkene | % Yield |
|---|---|---|
| 4-(4-tert-butylcyclohex-1-en-1-yl)morpholine | 4-tert-butylcyclohexene | 72 |
| 1-(6-cyclohexylcyclohex-1-en-1-yl)pyrrolidine | cyclohexylcyclohexene | 75 |
| 1-(6-phenylcyclohex-1-en-1-yl)pyrrolidine | phenylcyclohexene | 69 |
| morpholine-substituted cyclohexanone ethylene ketal enamine | cyclohexanone ethylene ketal alkene | 75 |
| 4-(5,6-dihydro-2H-thiopyran-3-yl)morpholine | 3,6-dihydro-2H-thiopyran | 65 |
| 4-(5,6-dihydro-2H-pyran-3-yl)morpholine | 3,6-dihydro-2H-pyran | 50 |

TABLE I-continued

| Enamine | Alkene | % Yield |
|---|---|---|
| 4-(1-benzyl-1,2,3,6-tetrahydropyridin-4-yl)morpholine | 1-benzyl-1,2,3,6-tetrahydropyridine | 85 |
| 1-(3,3,5,5-tetramethylcyclohex-1-en-1-yl)piperidine | 1,1,3,3-tetramethylcyclohex-4-ene (3,3,5,5-tetramethylcyclohexene) | 68 |
| (E)-4-(non-1-en-1-yl)morpholine [CH₃(CH₂)₆CH=CH–N(morpholine)] | (E)-1-octene / non-1-ene [CH₃(CH₂)₆CH=CH₂] | 80 |
| (E)-4-(3-phenylprop-1-en-1-yl)morpholine [PhCH₂CH=CH–N(morpholine)] | (E)-3-phenylprop-1-ene (allylbenzene) [PhCH₂CH=CH₂] | 82 |
| 1-[(1E,3E)-deca-... dienyl]azepane [CH=CH–(CH₂)₇–CH=CH–N(azepane)] | corresponding diene [CH=CH–(CH₂)₇–CH=CH₂] | 72 |
| (1E,3E)-morpholinyl pentadecadienyl enamine [CH₃(CH₂)₄CH=CH–CH₂–CH=CH–N(morpholine)] | (1E,3E)-diene [CH₃(CH₂)₄CH=CH–CH₂–CH=CH₂] | 82 |
| (morpholinyl dienyl enamine with CH₃(CH₂)₄-) | (CH₃(CH₂)₄CH=CH–CH₂–CH=CH₂) | 89 |
| 1-(6-methylcyclohex-1-en-1-yl)pyrrolidine | 3-methylcyclohex-1-ene | 70 |

TABLE I-continued

| Enamine | Alkene | % Yield |
|---------|--------|---------|
| [structure: pyrrolidine enamine with isoprenyl chain] | [structure: diene with isoprenyl chain] | 75 |

The data shown in Table I above demonstrates the broad utility of the method of this invention for the preparation of alkenes by the hydroboration of enamines followed by elimination under mild conditions. The preparation of terminal alkenes, dienes and heterocyclic alkenes in which the heteroatom is oxygen, sulfur or substituted nitrogen is demonstrated.

EXAMPLE 3

Preparation of [Z]-1-Phenyl-1-Propene

To a stirred suspension of 2.44 g (20.0 mmoles) of 9-borabicyclo[3.3.1]nonane (9-BBN) in 2 ml of tetrahydrofuran (THF) at 25° C. is added 4.06 g (20.0 mmoles) of [E]-1-morpholino-1-phenyl-1-propene. After three hours at 25° C., the reaction mixture becomes a clear solution. The absence of 9-BBN in the reaction solution is confirmed by $^{11}B$ NMR spectroscopy.

The THF is removed under a pressure of 12 Torr. The reaction flask is then fitted with a distillation head and 0.62 g (20.0 mmoles) of methanol is added. A mildly exothermic reaction occurs and the reaction mixture solidifies. The solid is melted with heating and [Z]-1-phenyl-1-propene and methanol are collected by distillation at atmospheric pressure. The methanol is removed from the distillate by treatment of the distillate with 1.0 g of anhydrous calcium chloride. The product, 1.90 g of [Z]-1-phenyl-1-propene, is purified by distillation. This is a yield of 81 percent based on the [E]-1-morpholino-1-phenyl-1-propene. The stereochemistry of the product is confirmed by $^1H$ and $^{13}C$ NMR spectroscopy. None of the [E] isomer is detected.

EXAMPLE 4

Preparation of [Z]-1,2-Diphenylethene

To a mixture of 1.22 g (10.0 mmoles) of solid 9-borabicyclo[3.3.1]nonane (9-BBN) and 2.66 g (10.0 mmoles) of [E]-1-morpholino-1,2-diphenylethene is added 5.0 ml of tetrahydrofuran (THF). The mixture is stirred at 25° C. for 12 hours. The THF is removed under a pressure of about 12 Torr at 25° C. at the end of the 12 hours. The residue is dissolved in 10 ml of methanol and stirred at 25° C. for an additional 12 hours. A by-product, 9-methoxy-9-borabicyclo[3.3.1]nonane morpholine complex crystallizes out of the reaction mixture and is separated by filtration. The methanol is evaporated from the filtrate and the residue is distilled under reduced pressure. The product, 1.17 g of [Z]-1,2-diphenylethene is produced in a yield of 65 percent based on the [E]-1-morpholino-1,2-diphenylethene. The product has a boiling point of 82° C.–84° C. at 0.4 Torr. The stereochemistry of the product is confirmed by $^1H$ and $^{13}C$ NMR spectroscopy. None of the [E] isomer is detected.

EXAMPLE 5

Preparation of Additional [Z] Isomers

The procedures outlined in Example 4 are repeated varying the identity of the enamine subjected to hydroboration and elimination. The results obtained are shown in Table II below.

TABLE II

| Enamine | Alkene | % Yield |
|---------|--------|---------|
| [1-morpholino-1-phenylpropene] | [Z-1-phenylpropene] | 80 |
| [1-morpholino-1,2-diphenylethene] | [Z-stilbene] | 65 |
| [1-morpholino-1-(2-thienyl)propene] | [Z-1-(2-thienyl)propene] | 68 |
| [1-morpholino-1-(4-pyridyl)propene] | [Z-1-(4-pyridyl)propene] | 60 |

The data in Table II above indicates the broad utility of the invented process in the preparation of the [Z] isomers to the essential exclusion of [E] isomers.

EXAMPLE 6

Preparation of 5,6-Dihydro-2H-Pyran

A solution of 3.38 g (20 mmoles) of 4-morpholino-5,6-dihydro-2H-pyran in 20 ml of diethyl ether is added to 2.44 g (20 mmoles) of solid 9-BBN. The 9-BBN slowly dissolves and the trialkylborane produced precipitates from the reaction mixture. After 3 hours, the diethyl ether is evaporated and 2 ml of methanol is added to the residue. An exothermic reaction occurs and B-(morpholino)-9-BBN crystallizes from the solution. The supernatant liquid is transferred to a distillation apparatus and 0.90 g (55 percent yield based on the 4-morpholino-5,6-dihydro-2H-pyran) of 5,6-dihydro-2H-pyran is distilled off. The boiling point of the product is 86° C.–88° C. at 760 Torr.

EXAMPLE 7

Preparation of 5,6-Dihyro-2H-Thiopyran

A solution of 3.70 g (20 mmoles) of 4-morpholino-5,6-dihydro-2H-thiopyran in 10 ml of tetrahydrofuran (THF) is added to 2.44 g (20 mmoles) of solid 9-BBN. A suspension results which becomes clear after stirring for 6 hours at 25° C. The THF is removed under reduced pressure (20 Torr) and 2 ml of methanol is added to the remaining solid. An exothermic reaction is initiated by gentle warming and results in a clear solution which is stirred. The stirring is stopped and the mixture is cooled slowly to crystallize the by-product, B-(morpholino)-9-BBN methanol complex. The solid is triturated with n-pentane (3×30 ml) and the combined pentane layers are washed successively with water (2×10 ml), 3N sodium hydroxide (3×6 ml), 3N hydrochloric acid (3×6 ml), and water (2×10 ml). The pentane layer is then dried and the pentane is removed under 20 Torr pressure. The residue is purified by distillation to give 1.30 g (65 percent yield based on 4-morpholino-5,6-dihydro-2H-thiopyran) of 5,6-dihydro-2H-thiopyran, boiling point 58° C.–60° C. at 20 Torr.

EXAMPLE 8

Preparation of 1-Benzyl-1,2,3,6-Tetrahydropyridine

A solution of 5.16 g (20 mmoles) of 1-benzyl-4-morpholino-1,2,3,6-tetrahydropyridine in 10 ml of tetrahydrofuran (THF) is added to 2.44 g (20 mmoles) of solid 9-BBN. A suspension results which becomes clear after stirring for 6 hours at 25° C. The THF is removed under reduced pressure (20 Torr) and 2 ml of methanol is added to the remaining solid. An exothermic reaction is initiated by gentle warming and results in a clear solution which is stirred. The stirring is stopped and the mixture is cooled slowly to crystallize the by-product, B-(morpholino)-9-BBN methanol complex. The solid is triturated with n-pentane (3×30 ml) and the combined pentane layers are washed successively with water (3×10 ml), 3N sodium hydroxide (3×6 ml) and water (2×10 ml). The pentane layer is evaporated. The residue is purified by distillation to give 2.90 g (85 percent yield based on 1-benzyl-4-morpholino-1,2,3,6-tetrahydropyridine) of 1-benzyl-1,2,3,6-tetrahydropyridine, boiling point 98° C.–100° C. at 1 Torr.

EXAMPLE 9

Preparation of 3-Cyclohexene-1-One Ethylene Ketal

A solution of 4.50 g (20 mmoles) of 4-morpholino-3-cyclohexene-1-one ethylene ketal in 10 ml of tetrahydrofuran (THF) is added to 2.44 g (20 mmoles) of solid 9-BBN. A suspension results which becomes clear after stirring for 6 hours at room temperature. The THF is removed under reduced pressure (20 Torr) and 2 ml of methanol is added to the remaining solid. An exothermic reaction is initiated by gentle warming and results in a clear solution which is stirred. The stirring is stopped and the mixture is cooled slowly to room temperature to crystallize the by-product, B-(morpholino)-9-BBN methanol complex. The solid is triturated with n-pentane (3×30 ml) and the combined pentane layers are washed successively with water (3×10 ml), 3N sodium hydroxide (3×6 ml) and water (2×10 ml). The pentane solution is dried and the pentane is evaporated under reduced pressure (20 Torr). The residue is purified by distillation to give 2.10 g (75 percent yield based on 4-morpholino-3-cyclohexene-1-one ethylene ketal) of 3-cyclohexene-1-one ethylene ketal, boiling point, 82° C.–84° C. at 20 Torr.

The preceding examples demonstrate the broad utility of the process of this invention in preparing a wide range of alkenes including cyclic, acyclic terminal or heterocyclic alkenes and dienes.

What is claimed is:

1. A process for preparing alkenes consisting essentially of two essential steps of
   (1) reacting an enamine wherein the enamine has an alkene portion which corresponds to an alkene selected from the group comprising cyclic alkenes, heterocyclic alkenes, acyclic alkenes, terminal alkenes and dienes with a hydroborating agent selected from the group consisting of borinane and compounds corresponding to the formula

$R^1R^2BH$ wherein $R^1$ and $R^2$ are separately in each occurrence $C_{5-20}$ hydrocarbyl under reaction conditions sufficient to form an intermediate organoborane; and
   (2) subjecting the organoborane formed in step (1) to an elimination reaction under reaction conditions sufficient to form the alkene corresponding to the alkene portion of the starting enamine.

2. The process of claim 1 wherein $R^1$ and $R^2$ are separately in each occurrence $C_{5-20}$ cyclic or branched aliphatic hydrocarbyl.

3. The process of claim 1 wherein the hydroborating agent is selected from the group consisting of 9-borabicyclo[3.3.1]nonane, dicyclohexyl borane, diisoamyl borane and borinane.

4. The process of claim 3 wherein the hydroborating agent is 9-borabicyclo[3.3.1]nonane.

5. The process of claim 1 wherein the elimination reaction step is a non-catalyzed elimination.

6. The process of claim 1 wherein the elimination step is catalyzed by the addition of an electron donating compound.

7. The process of claim 7 wherein the elimination step is catalyzed by the addition of methanol.

8. The process of claim 7 wherein the elimination step occurs in at least about 10 minutes and no greater than about two hours.

9. The process of claim 8 wherein the elimination step occurs in about one hour.

10. The process of claim 1 wherein the elimination step is conducted in the absence of external heating.

11. The process of claim 1 wherein the reaction mixture in step (3) is heated to no more than about 50° C.

12. The process of claim 1 wherein the reaction mixture in step (3) is heated to no more than about 35° C.

13. The process of claim 1 wherein the alkene prepared is a diene.

14. The process of claim 1 wherein the alkene prepared has [E] and [Z] isomeric forms.

15. The process of claim 14 wherein the [Z] isomer of the alkene is formed essentially to the exclusion of the [E] isomer.

16. The process of claim 1 wherein the alkene prepared is a terminal alkene.

17. The process of claim 1 wherein the hydroboration is conducted in the presence of a solvent.

18. The process of claim 17 wherein the solvent is tetrahydrofuran.

19. A process for preparing an alkene comprising adding equimolar portions of an enamine and 9-borabicyclo[3.3.1]nonane in tetrahydrofuran to a reaction vessel; stirring the mixture at room temperature for six hours; removing the tetrahydrofuran under vacuum; adding a portion of methanol equimolar to the starting enamine and 9-borabicyclo[3.3.1]nonane; and recovering the product alkene by distillation.

* * * * *

UNITED STATES PATENT AND TRADEMARK OFFICE
CERTIFICATE OF CORRECTION

PATENT NO. : 4,895,996

DATED : January 23, 1990

INVENTOR(S) : Christian T. Goralski, Bakthan Singaram, Herbert C. Brown

It is certified that error appears in the above-identified patent and that said Letters Patent is hereby corrected as shown below:

On the cover page, in the 5th line of the ABSTRACT "9-borabi-cyclo[3.3.1 nonane" should read -- 9-borabicyclo[3.3.1]nonane --.

Col. 14, line 47, Claim 7, "The process of Claim 7" should read -- The process of Claim 6 --.

Signed and Sealed this

Twenty-third Day of April, 1991

Attest:

HARRY F. MANBECK, JR.

Attesting Officer

Commissioner of Patents and Trademarks